US011986247B2

(12) United States Patent
Abbaschian et al.

(10) Patent No.: US 11,986,247 B2
(45) Date of Patent: May 21, 2024

(54) ROBOTIC JOINT REVISION SYSTEM AND METHOD

(71) Applicant: Revision Robotics Surgical Innovations, LLC, Frisco, TX (US)

(72) Inventors: Cyrus Abbaschian, Frisco, TX (US); Joshua Haney, Frisco, TX (US); Jeff Fox, Frisco, TX (US)

(73) Assignee: Revision Robotics Surgical Innovations, LLC, Frisco, TX (US)

(*) Notice: Subject to any disclaimer, the term of this patent is extended or adjusted under 35 U.S.C. 154(b) by 546 days.

(21) Appl. No.: 17/201,976

(22) Filed: Mar. 15, 2021

(65) Prior Publication Data

US 2021/0282859 A1    Sep. 16, 2021

Related U.S. Application Data

(60) Provisional application No. 62/989,390, filed on Mar. 13, 2020.

(51) Int. Cl.
*A61B 34/10* (2016.01)
*A61B 17/14* (2006.01)
(Continued)

(52) U.S. Cl.
CPC ............ *A61B 34/10* (2016.02); *A61B 17/142* (2016.11); *A61B 17/16* (2013.01); *A61B 34/20* (2016.02);
(Continued)

(58) Field of Classification Search
CPC ....... A61B 34/10; A61B 17/142; A61B 17/16; A61B 34/20; A61B 34/25; A61B 34/30; A61B 2034/104; A61B 2034/105
See application file for complete search history.

(56) References Cited

U.S. PATENT DOCUMENTS 5,041,120 A * 8/1991 McColl .............. A61B 17/8847
606/100
2021/0315640 A1* 10/2021 Dees, Jr. ............ A61B 17/1767

OTHER PUBLICATIONS

Thinwheel with Reuseable Mandrel (resin bond), Diacut Thinwheel, https://diacut.com/thinwheel-with-reusable-mandrel-2/ (Year: 2017).*

(Continued)

*Primary Examiner* — Tammie K Marlen
*Assistant Examiner* — Maria Catherine Anthony
(74) *Attorney, Agent, or Firm* — Polsinelli PC; Adam C. Rehm

(57) ABSTRACT

Systems and methods for prosthetic implant revision surgery may include a robot having a robotic arm for attaching multiple surgical tools. The robot may generate a surgical plan for attaching the surgical tools to the robotic arm (e.g., a large diameter wheel, an in-line cutting tip, a posterior curved cradle, a reciprocal saw, a long burr, a trephine reamer, an osteotome, a keel remover, etc.) and performing the steps to remove an anterior flange/cap of a prosthetic knee and debond cement from bone within the intramedullary canal of a tibia or femur. The robot may include cameras and/or tracking devices for mapping/generating a three-dimensional model of an operating space and the implant, and determine precise planes and angles for approaching the implant with the surgical tools. Accordingly, the systems and methods may perform revision surgery with less bone loss than previous techniques and may result in more reproducible outcomes.

16 Claims, 8 Drawing Sheets

(51) Int. Cl.
  *A61B 17/16*   (2006.01)
  *A61B 34/00*   (2016.01)
  *A61B 34/20*   (2016.01)
  *A61B 34/30*   (2016.01)
  *A61B 90/00*   (2016.01)

(52) U.S. Cl.
  CPC .............. *A61B 34/25* (2016.02); *A61B 34/30* (2016.02); *A61B 90/36* (2016.02); *A61B 2034/104* (2016.02); *A61B 2034/105* (2016.02); *A61B 2034/2057* (2016.02)

(56) References Cited

OTHER PUBLICATIONS

Brassler Large Bone Reciprocating Saw Blades, Medline, https://www.medline.com/sku/item/MDPKOMKM278N, (Year: 2018).*
Othopedic Burr DR, Chongqing Xishan Science & Techology, Medical Expo, https://www.medicalexpo.com/prod/chongqing-xishan-science-technology/product-121460-952786.html (Year: 2015).*

* cited by examiner

ROBOTIC JOINT REVISION SYSTEM AND METHOD

CROSS-REFERENCE TO RELATED APPLICATION

The present application claims benefit under 35 U.S.C. § 119 to U.S. Provisional Patent Application Ser. No. 62/989,390, entitled "Robotic Joint Revision System and Method" and filed on Mar. 13, 2020, which is incorporated by reference herein in its entirety.

BACKGROUND

1. Field of the Invention

The present inventive concept relates generally to systems and methods for robotic joint revision surgery and more particularly, to removing a previously implanted prosthetic joint from a bone.

2. Discussion of Related Art

Joint revision is a surgical procedure performed to improve function of a previously implanted prosthetic joint (e.g., to improve balance or alignment), treat an infection caused by the previous joint replacement, or to address implant failure such as loosening. Joint revision surgery typically involves removal of the previous prosthetic joint and implanting of a new prosthetic joint. For example, knee joint revision surgery may involve removing a tibial and/or femoral component of a previous prosthetic knee joint. Hip joint revision surgery may involve removing a femoral and/or acetabular component of a previous prosthetic hip joint.

Joint revision surgery is different from primary joint replacement surgery. In particular, joint revision surgeries are more difficult and complex procedures and require extensive planning and specialized tools. For example, removal of the previous prosthetic implant involves a step of debonding the previous prosthetic implant from the bone of the patient. The step of debonding must be performed with precision in order to preserve as much of the patient's bone as possible.

However conventional tools and approaches for performing joint revision surgeries are deficient in a number of areas. In particular, the precision attainable via conventional tools and approaches for joint revision surgery is limited. For example, visualization inside the intramedullary canal of a femur or tibia is limited in conventional approaches for joint revision surgery, thereby decreasing the precision attainable via such approaches. Conventional procedures also rely on multiplane fluoroscopy to guide the trajectory of surgical tools, for example, when debonding a cemented stem from bone. This complicates the procedure because it is a slow process due to resistance from the metal stem. Additionally, limitations in the accuracy and precision attainable with conventional tools used for the debonding step in joint revision procedures further decreases the ability of surgeons to preserve bone integrity. For example, because the cement bonding the previous prosthetic joint to a bone is often harder than the surrounding bone, debonding of the previous prosthetic joint from the bone via conventional handheld tools i.e., traditional mallet strikes, osteotomes, burrs, oscillating saws, metal cutting tools, and reamers, can lead to breaking through the bone cortex, resulting in loss of bone integrity and additional challenges to the procedure. In particular, studies have shown that the strikes of a conventional handheld surgical mallet produce an inconsistent amount of force, leading to complications in setting the new joint implant.

The present inventive concept remedies these deficiencies.

SUMMARY

The present inventive concept provides systems and methods for robotic joint revision surgery.

The systems and methods of the present inventive concept may utilize a robot configured to assist a surgeon in performing a robotic joint revision, the robot including a robotic arm operable to interchangeably connect with one or more specialized surgical tools for performing a joint revision surgery. In some instances, the system may use a particular sequence of surgical tools for performing the joint revision surgery. The particular sequence of surgical tools may correspond to a particular type of prosthetic implant to be removed (e.g., a prosthetic knee joint) and/or a geometry of the particular type of prosthetic implant. The system may a particular sequence of surgical steps corresponding to the particular sequence of tools and/or to the particular type of prosthetic implant. For instance, the one more surgical steps of the sequence may comprise one or more motions along a three-dimensional planes and/or at different angles such that the system may perform multiple different steps with the sequence of surgical tools to remove the prosthetic implant with minimal bone loss and/or tissue damage.

In one implementation, the system may include a robot may having a plurality of components coupled via a connection. The plurality of components may include a robotic arm. The plurality of components may include a processing unit. The plurality of components may include a non-transitory computer readable medium, such as memory, for storing instructions to be executed by the processing unit. The plurality of components may include one or more output devices, such as a display monitor. The robotic arm is another example of an output device. The plurality of components may include a plurality of input devices for detecting and communicating information to the robot, for example, a plurality of sensors. The plurality of components may further include and an input/output interface in connection with the one or more output devices and the plurality of input devices for governing and managing input and output.

The system may include one or more specialized surgical tools interchangeably in connection with the robotic arm. For instance, the robotic arm may include a specialized tool attachment mechanism (e.g., "connector") shaped for attaching to a first tool, releasing the first tool, attaching to a second tool, releasing the second tool, attaching to the third tool, releasing the third tool, etc. The connector may be configured to mate with and/or release a plurality of tools, such as one or more specialized surgical tools, used throughout the sequence of surgical steps. The one or more specialized surgical tools in connection with the robotic arm may include a large diameter wheel, an in-line cutting tip, a posterior curved cradle, a reciprocal saw, a long burr operable to debond cement from bone within the intramedullary canal of a tibia or femur, a hemispherical or ⅓ trephine reamer, a small osteotome, a curved or circular osteotome, a vibrator attachment, a bonding rotary tool, a keel remover, a motion converter, and/or an instrument operable to melt cement. In some instances, the one or more specialized tools may include one or more unique identifiers by which the system determines the type and/or dimensions of the specialized tools (e.g., by using one or more cameras to detect the one or more unique identifiers). For instance, the system may store specifications of the specialized tools (which may be provided by a manufacturer of the specialized tools) associated with the unique identifiers in a database Additionally or alternatively, the system may store one or more geometric profiles of the specialized surgical tools for comparing with tools in view of the one or more cameras to determine a type and/or dimension of the tools.

The robot may be configured to execute instructions stored in the non-transitory computer readable medium, via the processing unit, in response to information transmitted to and from the output and input devices. For example, the robot may be configured to recognize, register, and navigate the one or more specialized surgical tools via the robotic arm.

Thus, the system is advantageous because the system's guided navigation allows for operation of the one or more surgical tools with a higher degree of accuracy and precision than conventional methods. It is foreseen that each of the one or more various surgical tools may be used in one or more steps of a method of the present inventive concept. The system may perform one or more methods. For instance, in one implementation, a method includes generating, via a robot having a robotic arm, a surgical plan for removing a previous prosthetic joint from a bone of a patient, the robotic arm may be configured to provide robot-assisted navigation based on the surgical plan generated. The surgical plan may be based at least in part on a plurality of two-dimensional and/or three-dimensional images of a limb of the patient having the previous prosthetic joint. The three-dimensional images may, in some instances, be provided to the robot prior to performing the joint removal procedure. For example, the robot may receive one or more of x-rays, computed tomology (CT) scans, magnetic resonance imagings (MRIs), or other medical imaging data representing the particular prosthetic implant and/or surrounding bones and tissue. From the two-dimensional and/or three dimensional images, the system may generate a three-dimensional model of the prosthetic implant (e.g., including metal, cement, and/or adhesives holding the prosthetic implant in place) and/or surrounding bone to map into a three-dimensional model of the operating space (e.g., surgery room).

In some examples, the method may include a sequence of steps for removing the prosthetic implant, such as a previously implanted prosthetic joint, using a robotic arm to reduce damage to the bone and surrounding tissue. For instance, the sequence of steps may include a first step of performing a standard athrotomy or opening in the skin and/or muscle tissue to expose the previously implanted prosthetic. The first step may be performed by attaching a first tool, which may comprise a blade or scalpel, to the robotic arm, and making one or more incisions to the skin and/or muscle tissue. The first step may comprise a tissue-cutting step. In some instances, the first step may be performed by a surgeon instead of the robot.

The sequence of steps may include a second step of operating a second tool. The second tool may comprise a large diameter cutting wheel in connection with the robotic arm to cut a first portion of a previously implanted prosthetic joint along a plane. The plane may comprise a substantially vertical plane, or an x-y plane, with respect to a three-dimensional coordinate system of the three-dimensional model of the operating space. The second step may comprise a first metal cutting and/or a first bone cutting step, for instance, along the vertical plane.

The sequence of steps may include a third step of operating a third tool. The third tool may comprise a long burr in connection with the robotic arm to break cement between the bone of the patient and the previously implanted prosthetic joint. For instance, the system may determine one or more angles (e.g., with respect to the three-dimensional coordinate system) to approach the cement with the burr, and one or more breaking motions of the long burr to remove the cement (e.g., a linear swiping motion, a circular motion, and/or reciprocate back-and-forth along the one or more axes). The third step may comprise a cement removal step.

The sequence of steps may include a fourth step of operating a fourth tool. The fourth tool may comprise a tapered drill in connection with the robotic arm. The fourth step may include determining one or more angles (e.g., with respect to the three-dimensional coordinate system) for approaching the previously implanted prosthetic joint with the tapered drill. The fourth step may comprise a second metal cutting step, a metal drilling step, a second bone cutting step, and/or a bone drilling step.

The sequence of steps may include a fifth step of operating a fifth tool. The fifth tool may comprise the long burr (e.g., which may be similar to or identical to the third tool of the third step) in connection with the robotic arm to drill into a second portion of the previously implanted prosthetic joint. The fifth step may include determining one or more angles (e.g., with respect to the three dimensional coordinate system) for approaching the previously implanted prosthetic joint with the long burr. The fifth step may comprise a metal removal and/or bone removal step.

The sequence of steps may include a sixth step of operating a sixth tool. The sixth tool may comprise a slap hammer, and the sixth step may comprise attaching the slap hammer to a tapered or conical drill with an adaptor bolt. The sixth step may comprise determining one or more angles (e.g., with respect to the x-y-z coordinate system of the three-dimensional model of the operating space) for approaching the previously implanted prosthetic joint, and extracting the second portion of the previously implanted prosthetic joint via the slap hammer. The sixth step may comprise a metal removal step.

In some instances, any of the steps of the sequence of steps may include a simultaneous operation of maintaining a cradle in proximity to the specialized tool being used for the step. For instance, the cradle may comprise a posterior curved cradle attached to the robotic arm (or a second robotic arm) that may protect soft tissue from metal debris and/or bone debris generated during a metal cutting step, metal drilling step, bone cutting step, and/or bone drilling step.

It is an objective of the system and method of the present inventive concept to increase accuracy and precision, thereby minimizing bone loss and improving patient outcomes in joint revision surgery.

It is an objective of the system and method of the present inventive concept to provide a system and method that is superior due to a system that utilizes specialized joint revision surgical tools and, in some instances, in a particular sequence.

It is an objective of the system and method of the present inventive concept to provide a system, e.g., robotic arm and a plurality of joint revision instruments operable to be used in connection with the robotic arm. Specifically compared to traditional systems and methods for joint revision surgery, the product of the present inventive increases accuracy and precision, thereby minimizing bone loss. These benefits greatly improve patient outcomes for patients of joint revision surgery.

BRIEF DESCRIPTION OF DRAWINGS

For the purposes of description, but not of limitation, the foregoing and other aspects of the present inventive concept are explained in greater detail with reference to the accompanying drawings, in which.

Figure 1:
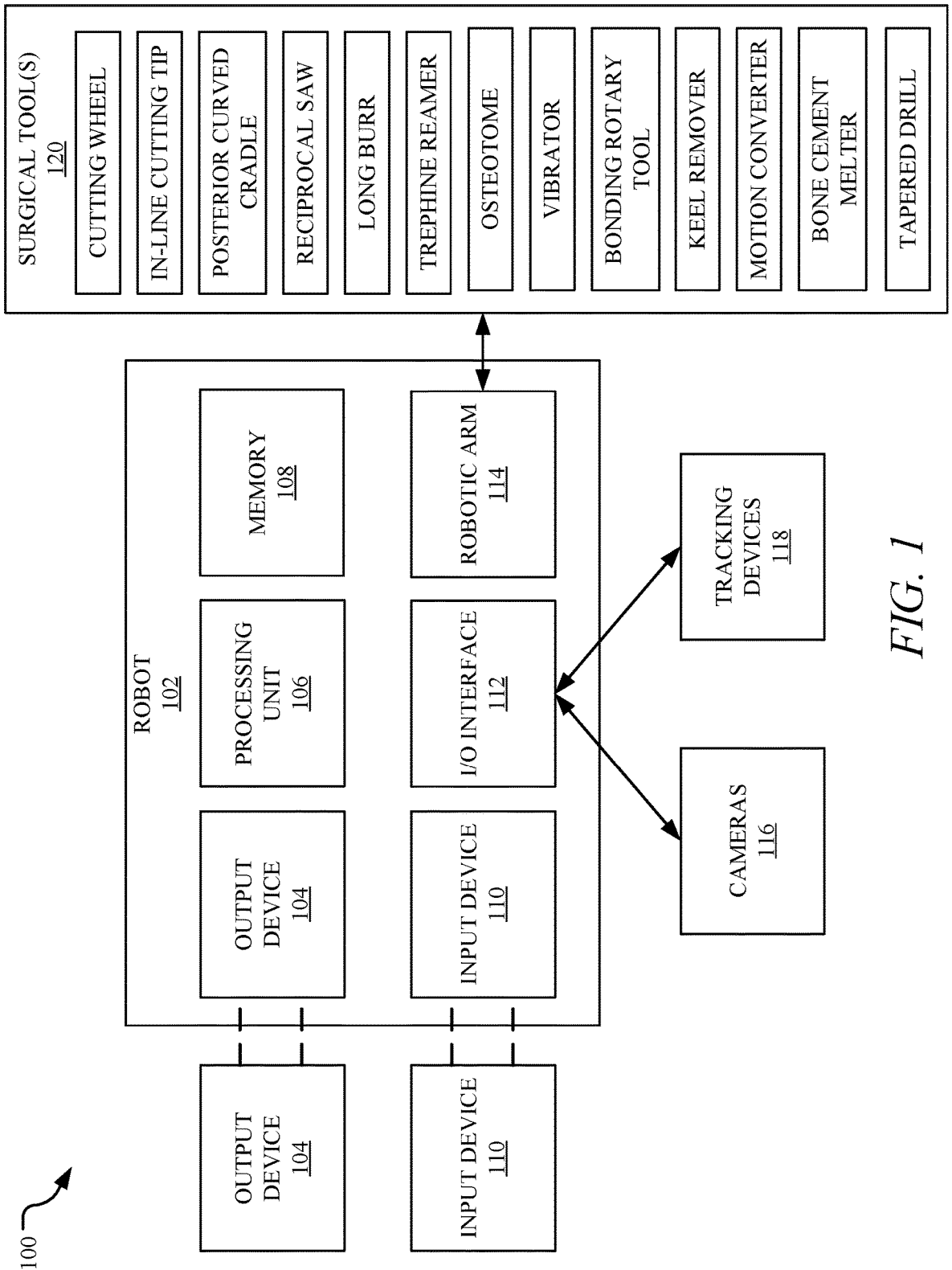
FIG. 1 is a functional block diagram illustrating an example system for robotic joint revision.

The drawings do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The systems and methods of the present inventive concept may utilize one or more various surgical tools in connection with a robotic arm of a robot configured to assist a surgeon in performing a robotic joint revision by providing guided navigation of the robotic arm. The robot may be configured to understand the geometry of the one or more various surgical tools and to register the robotic arm to understand the location of the tool in a space and/or relative to other objects in a space. Thus, the robotic arm allows for navigation of the one or more surgical tools with a higher degree of precision than conventional methods. It is foreseen that each of the one or more various surgical tools may be used in one or more steps of a method comprising the sequence of steps. It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The systems and methods described herein are constructed to overcome the major disadvantages involved in conventional joint revision procedures. The systems and methods herein may have improved accuracy, precision, and better patient outcomes as compared to the current state of the art.

A description of a system 100 for robotic joint revision, as illustrated in FIG. 1, is disclosed herein. The system 100 may include a robot 102 having a robotic arm 114 and one or more surgical tools 120 in connection with the robotic arm 114. The robotic arm 114 may be configured to provide robot-assisted navigation of the one or more surgical tools 120.

The robot 102 may include a plurality of components. The plurality of components may include a robotic arm 114. The plurality of components may include a processing unit 106. The plurality of components may include a non-transitory computer readable medium, such as memory 108, for storing instructions to be executed by the processing unit 106.

The plurality of components may include one or more output devices 104, such as a display monitor. The robotic arm 114 is another example of an output device. Each of the one or more output devices 104 may be integral to or separate from the robot 102. The one or more output devices allow the robot 102 to navigate the one or more surgical tools 120.

The plurality of components may include a plurality of input devices 110 for detecting and communicating information to the robot 102. For example, the plurality of input devices 110 may include an accelerometer, a gyroscope, a tracking ray, a plurality of cameras 116, and/or a plurality of tracking devices 118. The plurality of tracking devices 118 may include a tension gauge, a muscle strain gauge, and/or a patella tracking device. The plurality of input devices are configured to detect information and transmit it to the robot 102. Such information may allow the robot 102 to recognize, register, and manipulate the one or more surgical tools 120 via the robotic arm 114. In other words, the plurality of input devices allow the robot 102 to understand the location of the one or more surgical tools 120 in a space and/or relative to other objects (e.g., the patient's limb). The robot 102 may be configured to execute, via the processor, instructions stored in system memory in response to input data obtained from the plurality of input devices. Each of the plurality of input devices may be integral to or separate from the robot 102 and/or the other components of the robot. Thus, the plurality of input devices allow for navigation of the one or more surgical tools 120 in connection with the robotic arm 114 with a higher degree of accuracy and precision than conventional methods.

The plurality of components may further include and an input/output interface 112 in connection with the one or more output devices 104, and the plurality of input devices for governing and managing input and output data.

The robot 102 may be configured to execute instructions stored in the non-transitory computer readable medium, via the processing unit, in response to information transmitted to and from the output and input devices. For example, the robot 102 may be configured to recognize, register, and navigate the one or more surgical tools 120 via the robotic arm 114.

The system may include the one or more surgical tools 120. The one or more surgical tools 120 may be in connection with the robotic arm 114. The one or more surgical tools 120 may be in connection with the input/output interface 110. The robot 102 may be configured to understand the various geometries of the one or more surgical tools 120 and to register the robotic arm 114 to understand the location of the tool in a space and/or relative to other objects in a space.

Thus, the robotic arm 114 allows for navigation of the one or more surgical tools 120 with a higher degree of precision than conventional methods.

Each of the one or more surgical tools 120 may be used in connection with the robotic arm 114 and/or the input/output interface to perform one or more steps of the method of the present inventive concept. The one or more surgical tools 120, which may comprise any of the tools discussed above (e.g., the first tool, the second tool, the third tool, the fourth tool, the fifth tool, or the sixth tool) may include:

A large diameter wheel, such as a carbide or diamond wheel operable to cut through a preexisting joint implant. In at least one example, the large diameter wheel may be in connection with the robotic arm 114 via a shank. In such an example, the shank and the large diameter wheel may be separate components fastened together via a bead or may be integral components without a fastening bead to allow for more precise cutting. In some examples, the diameter of the large diameter wheel is larger than the diameter of conventional carbide or diamond surgical wheels. In such examples, the diameter of the large diameter wheel may be greater than 25.4 mm. In at least one example, the large diameter wheel has a diameter of 40-50 mm. The large diameter wheel is advantageous over conventional carbide or diamond surgical wheels because it increases wheel cutting depth to allow access to portions of the preexisting joint implant 2-3 cm deep from an anterior surface of the preexisting joint implant. In at least one example, the large diameter wheel may be used in one or more steps of a method for robotic revision of a preexisting femoral joint implant. In such examples, the large diameter wheel in connection with the robotic arm 114 may be used to cut through a portion of a femoral component of the preexisting implant to gain access to a stem of the preexisting implant within a bone canal of a patient An in-line cutting tip, operable to break through cement pedestals. It is foreseen that the in-line cutting tip used in connection with the robotic arm 114 is advantageous because it allows for increased precision in debonding or removing the previous prosthetic. Non-limiting examples of the in-line cutting tip include an Orthofix® Oscar™ probe.

A posterior curved cradle operable to be placed posterior to a curved portion of the previous prosthetic being cut. Such a tool used in connection with the robotic arm 114 is advantageous because it protects soft tissue of the patient. The posterior cradle may be further operable to assist in suction or irrigation by reducing metal debris. In at least one example, the posterior curved cradle may be used in connection with the large diameter wheel to improve safety while cutting.

A reciprocal saw operable to cut metal. In at least one example, the reciprocal saw is configured to provide a high reciprocating rate. In some examples, the reciprocal saw includes a small distal of excursion. In some examples, the reciprocal saw includes a carbide or diamond coating sufficient to cut through cobalt chrome. In at least one example, the reciprocal saw has a thickness of at least 1.89 mm. Performing joint revision using the reciprocal saw in connection with the robotic arm 114 allows for increased precision over conventional rotary cutting tools used in joint revision.

A long burr operable to debond cement from bone within the intramedullary canal of a tibia or femur. Performing joint revision using the long burr in connection with the robotic arm 114 allows the burr to be used deeper in the intramedullary canal than in conventional procedures because of the increased precision in navigating the tool via the robotic arm 114. With robotic navigation longer burrs can be used to remove cement as the navigation aspect will know where this cement is in space to safely use these tools within the bone canal. It is foreseen that the burr may have a sufficient diameter and length to control tool chatter. For example, as the burr length increases, the diameter of the burr may be increased to control tool chatter. In at least one example, the long burr has a length of 120-135 mm.

A hemispherical or ⅓ trephine reamer operable to debond a cemented stem from bone and/or press fit a stem from the bone. The hemispherical or ⅓ trephine reamer in connection with the robotic arm 114 is advantageous for debonding cemented stems because it reduces resistance compared to conventional techniques and allows for more precise navigation for cement removal and stem debonding. With navigation a $⅓^{rd}$ trephine reamer could be used to reduce resistance from the stem while using the navigation technique to guide the tool for cement removal and stem debonding. It is foreseen that the hemispherical or ⅓ trephine reamer may or may not have grooves to allow for particulate debris to be removed from the wound bed and to keep a tip of the reamer clear of cement dust and debris.

A small osteotome operable to chip away at cement. The small osteotome used in connection with the robotic arm 114 is operable to provide axial in-line intermittent pressure strikes simulating a mallet strike with controlled force and greater precision than is attainable with conventional approaches involving handheld mallet strikes.

A curved or circular osteotome operable to remove cement via a chiseling technique guided by navigation via the robotic arm 114. The curved or circular osteotome used in connection with the robotic arm 114 allows use of the osteotome in the intramedullary canal.

A vibrator attachment operable to attach to a retained implant or implant stem and provide high speed vibration to aid in debonding the implant from the bone. Such vibration may allow final debonding with minimal damage to the bone.

A tracking ray operable to orient the robot 102 to the body of the patient. It is foreseen that the ray may be expandable to cover a field of view, the field of view being sufficient to view the entire limb. The tracking ray includes multiple arrays to allow the robotic arm 114 to understand the location of the limb in space.

A plurality of cameras operable to record data over a field of view, the field of view being sufficient to identify the entire limb being operated on during the joint revision surgery.

A strain gauge operable to attach to a muscle and gauge the strain of the muscle during the joint revision procedure and detach from the muscle after completion of the procedure. Information regarding muscle strain is useful for understanding how a knee replacement revision will perform dynamically. If there is too much strain on the quadriceps muscle for example, regaining full flexion may not be possible. The strain gauge is advantageous because it helps predict optimum implant functioning, thus improving patient outcomes. The data generated from the strain gauge is communicated to the robot 102 for data analysis during the procedure.

A tension gauge operable to generate tension on a muscle through a passive range of motion and record data on the tension generated. The data is communicated to the robot 102 for interpretation. The data can be used to change variables throughout the procedure to improve function of the joint. For example, based on such data, soft tissue can be resected or tightened, implant position can be changed, and/or limb length can be changed based on this information to optimize function.

A patella tracking device operable to record data about patella function. Often for revision joint replacement surgery, management of the soft tissue around the patella is necessary to ensure optimum knee function. Also, by generating information of medial or lateral pressure, motion, trajectory through passive range of motion, and/or tilt on the patella to identify optimum patella tracking will help guide variables such as implant rotation, patella cut trajectory, polyethylene thickness, and soft tissue balancing.

A device for generating data from the strain, tension, and patella tracking devices and transmitting the data to the robot 102.

A bonding rotary tool operable to bond a retained implant to a striking platform. In some examples the bonding rotary tool bonds the implant to the striking platform by cold welding the retained implant to the striking platform. In some examples the bonding rotary tool bonds the implant to the striking platform by creating threads for attachment between the retained implant and the striking platform. The striking platform can be struck to remove the implant via a handheld mallet or a mallet in connection with the robotic arm 114.

A keel remover operable to remove the retained keel.

A motion converter operable to turn oscillating motion of a tool into revolution or axial intermittent motion.

An instrument operable to melt cement. It is foreseen that the instrument may use hypersonic vibrations, such as an Orthofix® Oscar™ probe.

The present inventive concept may utilize various methods. In one instance of the present inventive concept, the robotic arm 114 may be used in connection with the one or more surgical tools 120 to perform a joint revision surgery.

The aforementioned may be achieved in another aspect of the present inventive concept by providing a method for robotic joint revision including the step of operating the robotic arm 114 in connection with the one or more surgical tools 120.

Figure 2:
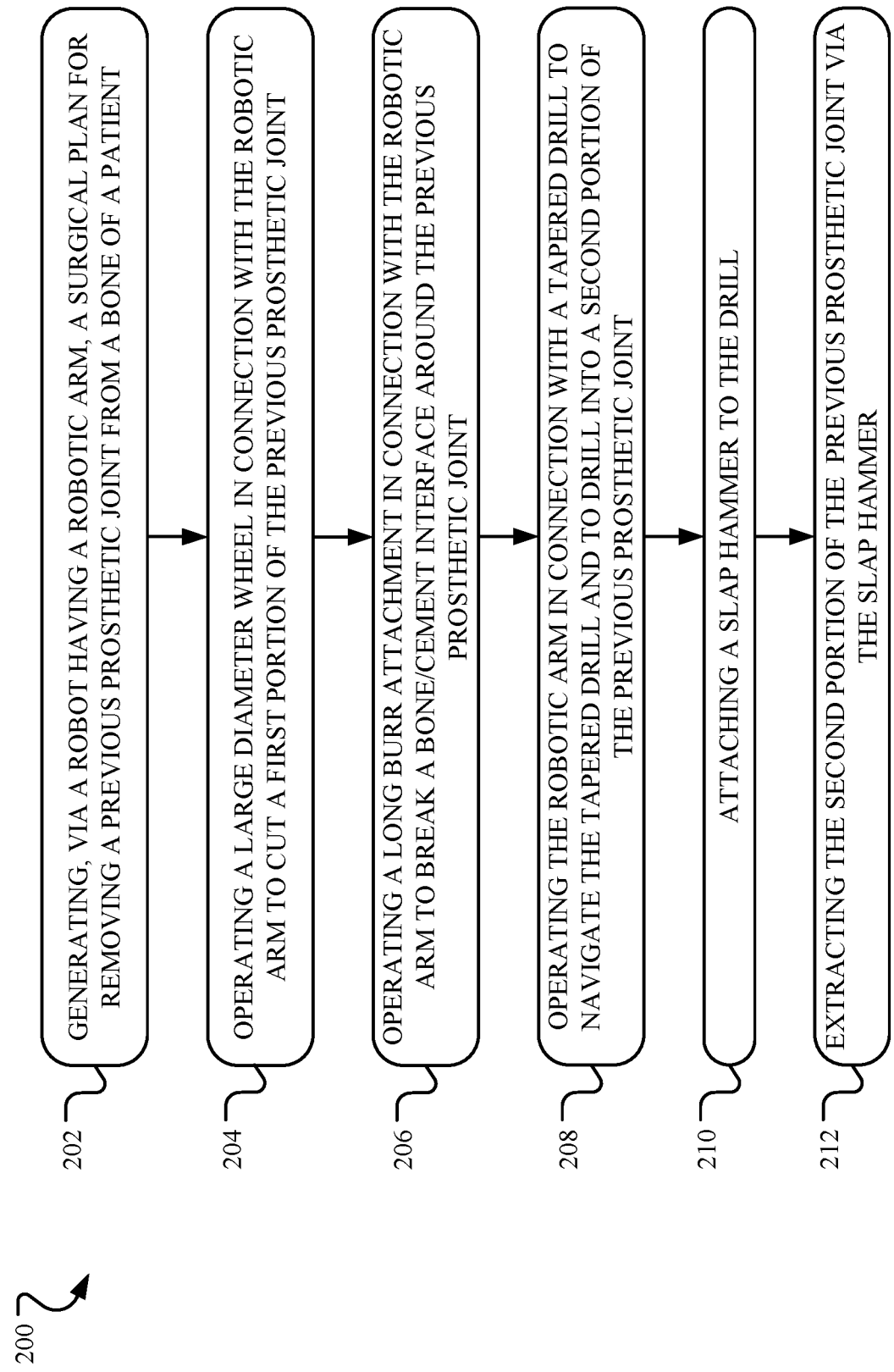
FIG. 2 is a flow chart illustrating an example method for robotic joint revision.

Turning to FIG. 2, a method 200 for performing robotic femoral joint revision is provided. The method 200 may comprise the sequence of steps using a particular sequence of the one or more surgical tools 120 for removing the previously implanted prosthetic joint. For instance, step 202 of method 200 may include generating, via the robot 102 having the robotic arm 114, a surgical plan for removing a previous prosthetic joint/implant from a bone of a patient. The robotic arm 114 may be configured to provide robot-assisted navigation based on the surgical plan generated. The surgical plan may be generated based on uploaded medical imaging data such as one or more of x-rays, CT scans, MRIs, or other medical imaging data provided to the system 100 and representing the particular prosthetic implant to be removed and/or surrounding bones and tissue. Step 204 may include operating a large diameter wheel in connection with the robotic arm 114 of the robot 102 to cut a first portion of a previous implant. In at least one example, the first portion may include a tibial tray of the previous prosthetic joint. Step 206 of method 200 may include operating a long burr in connection with the robotic arm 114 to break a bone/cement interface around the previous implant. Step 208 of method 200 may include operating a tapered drill in connection with the robotic arm 114 to drill into a second portion of the previous implant. In some examples, the second portion of the previous implant may include a keel of the previous implant. Step 209 of the method 200 may include attaching a slap hammer to the drill. The drill may be a conical or tapered drill. In some examples, step 209 may include attaching an adaptor bolt to the drill. In such examples, the slap hammer is attached to the adaptor bolt. Step 210 of the method 200 may include extracting the second portion of the previous implant via the slap hammer. In some examples, the method 200 may include the step of operating the robotic arm 114 in connection with a reamer, such as a ⅓ trephine reamer, to cut around a stem of the previous implant. In some examples, the method may include receiving input data, at the robot 102, via a plurality of input devices. In such examples, the method may further include generating changes to the surgical plan based on the input data received from the plurality of input devices.

Figure 3:
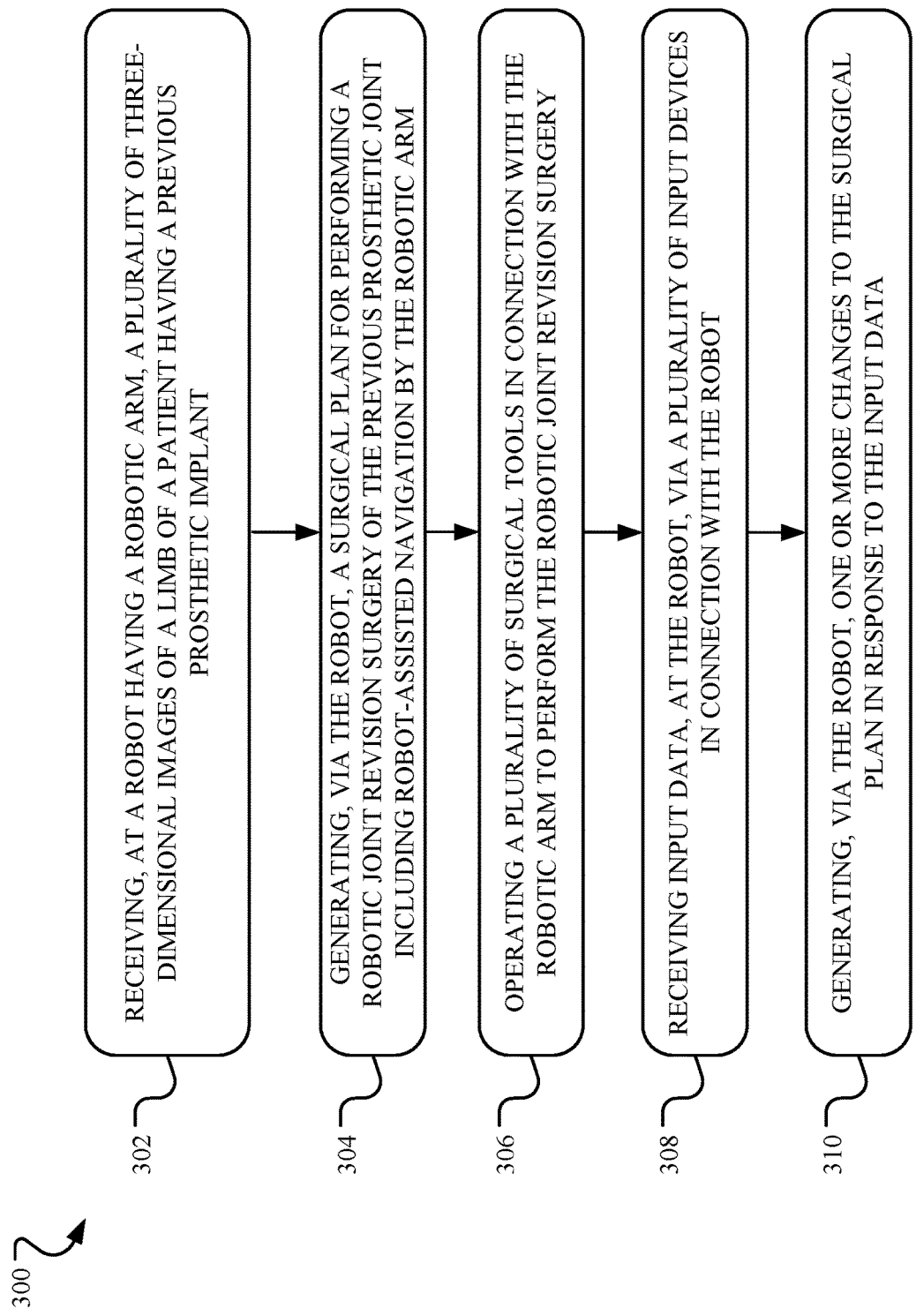
FIG. 3 is a flow chart illustrating an example method for robotic joint revision.

Referring to FIG. 3, an example method 300 for performing robotic joint revision is provided. The method 300 is provided as follows. Step 302 of method 300 may include receiving, at the robot 102 having the robotic arm 114, a plurality of three-dimensional images of a limb of the patient having a previous prosthetic implant. Step 304 of the method 300 may include generating, via the robot 102, a surgical plan for performing a robotic joint revision surgery of the previous prosthetic joint. The surgical plan may include robot-assisted navigation by the robotic arm 114 of the robot 102. Step 306 may include operating a plurality of surgical tools 120 in connection with the robotic arm 114 to perform the robotic joint revision surgery via the robot-assisted navigation and within the parameters of the surgical plan. In some examples, the method 300 may include step 308 receiving input data, at the robot 102, via a plurality of input devices in connection with the robot 102. In such examples, the method 300 may further include step 310 generating, via the robot 102, one or more changes to the surgical plan in response to the input data.

Figure 4:
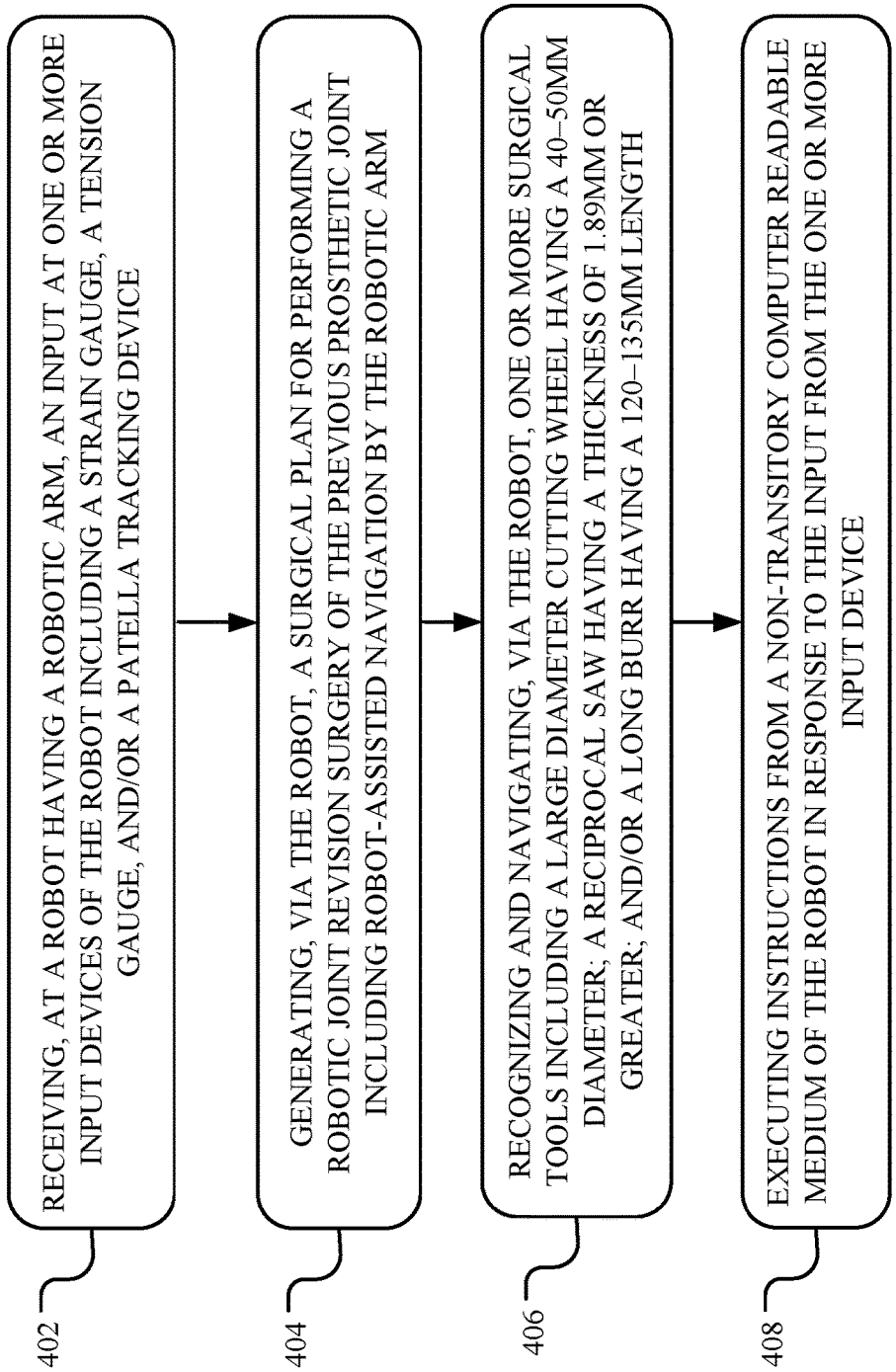
FIG. 4 is a drawing illustrating an example method for robotic joint revision.

Referring to FIG. 4, an example method 400 for performing robotic joint revision is provided. The method 400 is provided as follows. Step 402 of method 400 may include receiving, at the robot 102 having the robotic arm 114, an input at the one or more input devices 110, which may include at least one of a stain gauge, a tension gauge, and/or a patella tracking device. Step 404 of the method 400 may include generating, via the robot 102, the surgical plan for performing the joint revision surgery of the previous prosthetic joint including robot-assisted navigation by the robotic arm 114. Step 406 of the method 400 may include recognizing and navigating, via the robot 102, the one or more surgical tools 120, such as a large diameter cutting wheel having a 40-50 mm diameter; a reciprocal saw having a thickness of 1.89 mm or greater; and/or a long burr having a 120-135 mm length. Step 408 of the method 400 may include executing instructions from a non-transitory computer readable medium (e.g., the memory 108) in response to the input from the one or more input device.

FIGS. 5-8 help illustrate the surgical procedure for extraction of any implant design on the market. The unique instruments created in conjunction with the robot 102 knowing where the tool is in space offers the surgeons intraoperative flexibility to remove hardware and preserve bone in any patient with more control than the offerings available today. The surgical incision and muscle disruption may be no different than that of a primary joint replacement exposure. FIGS. 4-8 illustrate one or more steps that may comprise the sequence of steps for removing a previously implanted prosthetic joint, for instance, by using the sequence of the one or more surgical tools 120 attached to the robotic arm 114, as discussed above. In some instances, FIGS. 4-8 may not illustrate every steps of the sequence of steps, in that the sequence of steps may include additional steps omitted from FIGS. 4-8. Moreover, any of the steps illustrated in FIGS. 4-8 may be combined, omitted, repeated, and/or performed using multiple robotic arms 114 operating together during the sequence of steps. The steps illustrated in FIGS. 4-8 may be performed by any of the systems (e.g., system 100) discussed herein.

Figure 5:
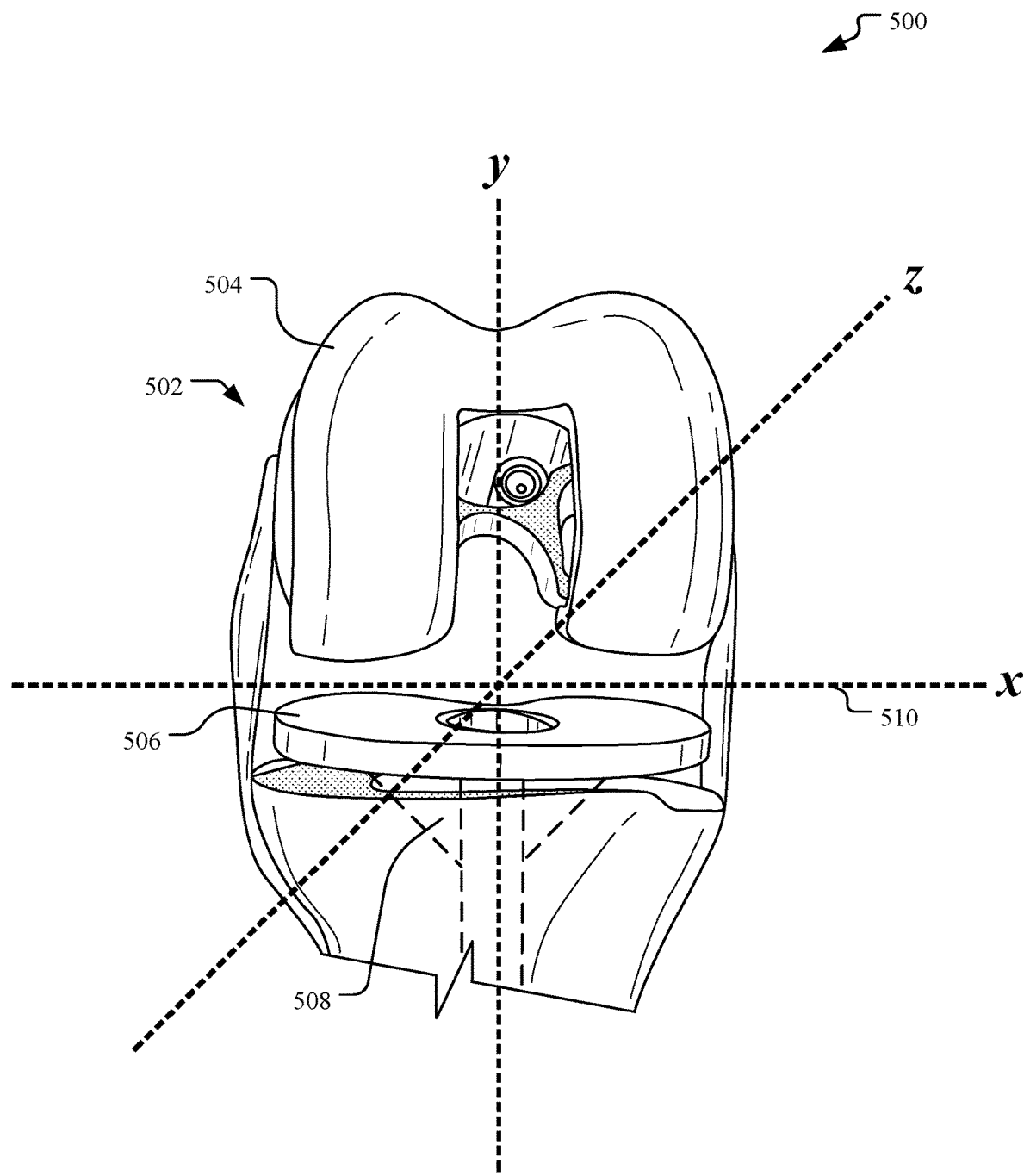
FIG. 5 is a drawing illustrating a step of an example method for robotic joint revision.

Referring to FIG. 5, a step 500 (e.g., the first step of the sequence of steps) for performing an example method for robotic joint revision is shown. In particular, FIG. 5 shows a step to be performed including or after a standard arthrotomy to obtain access to a previous prosthetic joint, illustrating what a surgeon will be looking at after removing the skin and/or muscle tissue. The intent for the use of robotics in the revision setting is to allow the surgeon to use a standard incision and arthrotomy as he would in a primary prosthetic implantation setting. The robot 102 has the ability to know where the tool and the previously implanted prosthetic joint are in space, thus allowing the surgeon to not have a larger dissection of the surrounding tissue to get the exposure to remove the primary implant/prosthesis. After incision and arthrotomy, the knee may be flexed and retractors may be put in for exposure to the knee. In some examples, the first step illustrated in FIG. 5 may include exposing and/or providing access to a previously implanted prosthetic knee 502. The previously implanted prosthetic knee 502 may include an anterior flange/cap 504 (e.g., a femoral component) and/or a tibial tray 506. The previously implanted prosthetic knee 502 may include a keel 508 connecting the tibial tray to a tibial stem extending down the intramedullary canal of a tibia. The first step may include the robot 102 establishing a three-dimensional coordinate system 510 (e.g., using the cameras 116, the tracking devices 118, and/or uploaded medical imaging data). The three-dimensional coordinate system 510 may comprise an x-axis, a y-axis, and a z-axis that the robot 102 may use as a reference for orienting the one or more surgical tools 120 and/or one or more motions of the one or more surgical tools 120 throughout an implant removal processes. In FIG. 5, the three-dimensional coordinate system 510 is illustrated with the y-axis extending vertically in a direction substantially parallel to a tibia of a patient and/or towards a ground plane and the x-axis extending horizontally across a front of the tibia and the anterior flange/cap 504, forming an x-y plane. The z-axis is illustrated extending perpendicular to the x-y plane. However, the robot 102 may establish any variation of the three-dimensional coordinate system 510 to align the axes of the three-dimensional coordinate system 510 along different anatomical structures and/or prosthetic joint structures. Moreover, the robot 102 may generate multiple three-dimensional coordinate systems 510 (e.g., and may calculate a translational relationship between the multiple three-dimensional coordinate systems 510) for mapping the anatomical structures and/or prosthetic joint structures to the three-dimensional model of the operating space.

Figure 6:
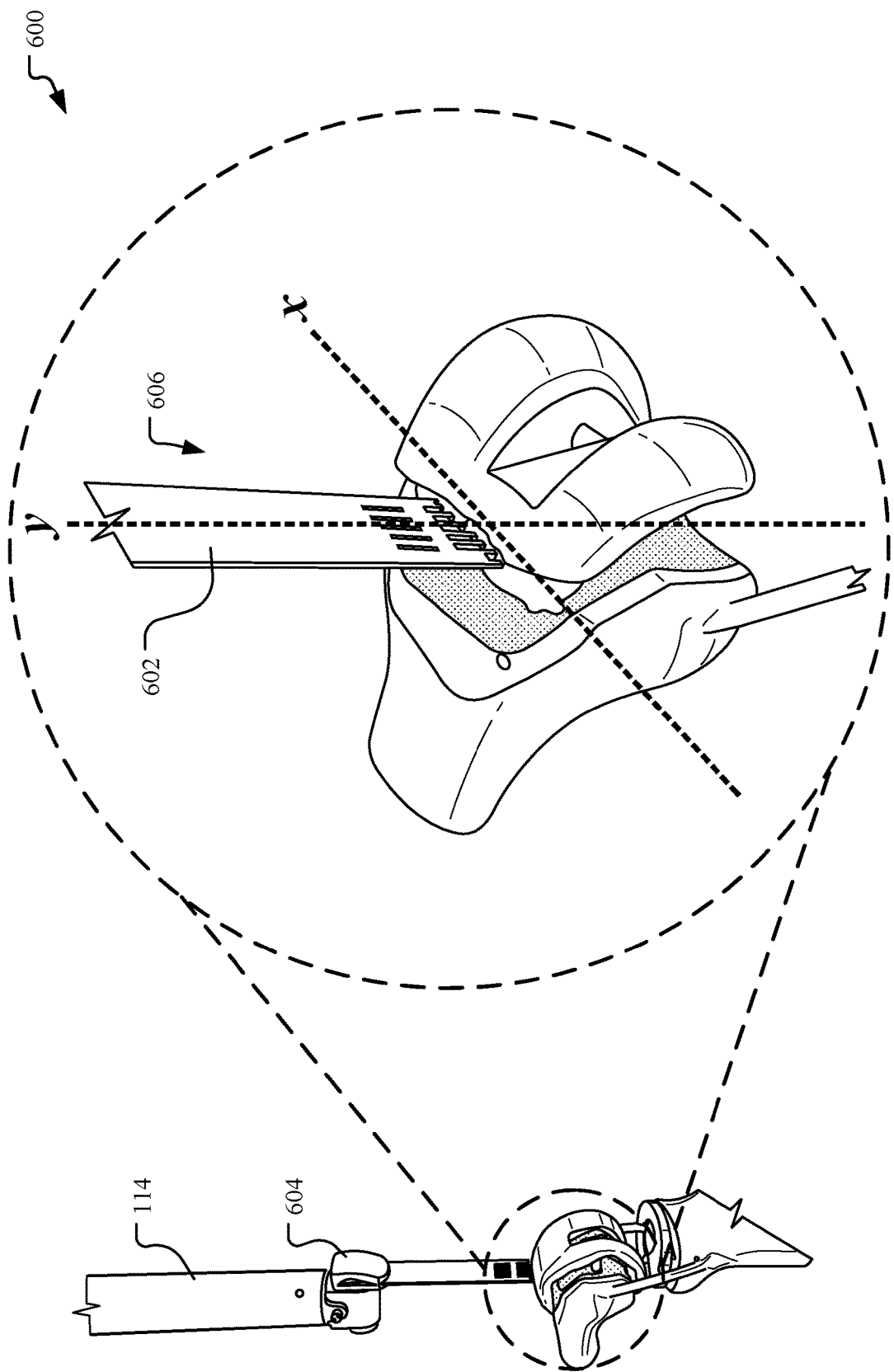
FIG. 6 is a drawing illustrating a step of an example method for robotic joint revision.

Turning to FIG. 6, a step 600 (e.g., the second step of the sequence of steps) for performing an example method for robotic joint revision is shown. FIG. 6 shows the cutting of the anterior flange/cap 504 of a previously implanted prosthetic knee 502 at the distal implant to bone interface and/or removal of the femoral component. In some examples, the anterior flange/cap 504 may be cut with an inline cutting tip 602 attached to the robotic arm 114 with a tool connector 604. The inline cutting tip 602 may be aligned along an x-y plane 606 of the three-dimensional coordinate system 510 and/or may move vertically downward on a portion of the anterior flange/cap 504. In some instances, a series of saws, burrs and osteotomes may be used to work around the femoral component to break the cement to bone interface or the cement to implant interface. With the robot 102, a surgeon can set the plane of the cutting devices to remove less bone and extract the implant based off of registration and implant thickness. In some examples, a metal cutting burr may be used to cut off the anterior flange/cap 504 and posterior condyles in a new planned resection plane. A cradle may capture the metal shavings so surrounding tissue is protected and a desired resection is achieved. This may allow the surgeon to preserve bone during the extraction portion of the procedure and better restore the joint line for the new implants. The major difference between this approach and current approaches used today is that the surgeon may not have to extend his incision up the quad muscle to gain access from the implant removal. The more quad muscle that is violated during the procedure creates a longer rehab for the patient to get the last 5-10 degrees of full/terminal extension. This is one of the chief complaints for patients post revision joint replacement. The ability to preserve the quad muscle may allow patients a recovery that is similar to primary joint replacement. In this image, the illustration utilizes a saw. However, the large diameter wheel or metal cutting reciprocating saw may be utilized for this step as well.

In some examples, the femoral component of the prosthetic implant may comprise a cruciate retaining (CR) implant design or a posterior stabilized (PS) implant design. The CR implant design may leave part of the anterior flange/cap 504 and posterior condyles attached, as well as femoral lugs, in which case the surgeon may use a straight burr, osteotome or saw to precisely removed the retained metal. For the lugs, a trephine or curette may be used with the robot 102 to precisely remove the retained metal. At this point, the desire resection and joint line may already be established for the new components based on an initial plan for reimplantation. An intramedullary (IM) reamer may be used to ream the femoral canal, and femoral cuts are made and a trial may be placed on the femur. The PS implant design may leave part of the anterior flange/cap 504 and posterior condyles, as well as a "box" of the femoral component. The surgeon may use a straight burr, osteotome or saw to precisely remove the retained metal. Historically, PS knees remove more bone from the end of the femur due to the cement around the box and the inability to use an instrument to debond the cement from the bone. With the method described herein, all cement on the component may be visible to the surgeon and/or robot 102 and be precisely removed with the described instrument. Once the component is removed, an IM reamer may prep the femoral canal, femoral cuts may be made and a trial may be placed on the femur. This illustrates some potential advantages of using the robot 102. One of the many challenges in a typical revision is restoring the joint line. With the approaches described herein of cutting through the implant, the joint line may be established by a series of registered point and sets the plane for optimal resection. A standard surgical saw is 1.27-1.35 mm thick. The saw or metal cutting burr may have a minimum thickness of 2 mm. This allows for a more controlled plane of the cut and the robot 102 can cut through sclerotic bone as well as cement. Thinner blades 1.27 and 1.35 mm may have a tendency to take the path of least resistance and "skive" which results in less precision and accuracy of the planned resection. Cement is harder than bone so the additional thickness may provide strength for the tool to stay in the cutting plane.

Figure 7:
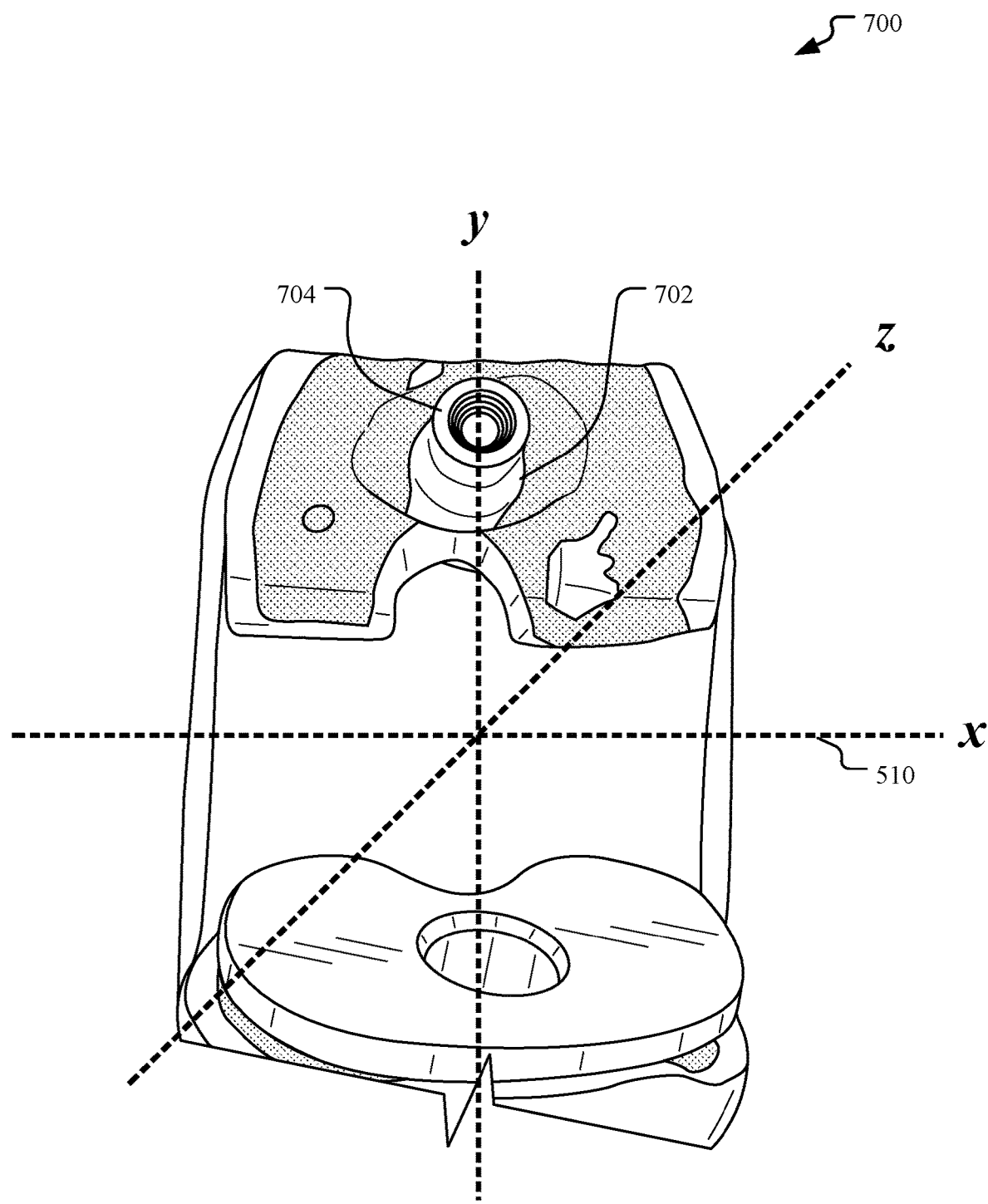
FIG. 7 is a drawing illustrating a step of an example method for robotic joint revision.

In FIG. 7, one or more steps 700 (e.g., the third step, the fourth step, and/or the fifth step of the sequence of steps) for performing an example method for robotic joint revision are shown. FIG. 7 shows what the surgeon and the robot 102 will be looking at after the anterior flange/cap 504 is removed from the bone. At this portion of the procedure, the surgeon may continue to use the large diameter wheel or the metal cutting reciprocating saw and continue down the implant to bone interface to remove the rest of the implant. In posterior stabilized design, the box of the implant will be left behind in the intercondular notch. At this point, the surgeon can use the inline cutting tip 602 to remove a cement/bone interface 702 within the notch and pull a retained metal stem 704 out with minimal bone loss. In Cruciate Retaining designs, the lugs of the primary femoral component will be left behind and the surgeon can use the inline cutting tip 602 to cut around the two retained lugs. This process will allow the surgeon to control the amount of bone loss with precision instruments for removal partnered with software capabilities of the robot 102 identifying the bone anatomy. Upon cutting the anterior flange/cap 504 of the previously implanted prosthetic knee 502 off of the boney interface, the surgeon may have a straight line of sight up or down the intermedullary canal. With the current implant offerings available, implanted stems up the canal are either cemented in the canal or they have surface enhancement or splines to dig into the cortical structure of the bone for added stability. At step 700, the surgeon and/or the robot 102 may have a straight line of sight to break the implant/bone or the cement/implant interface with the long in-line cutting burr or the $\frac{1}{3}^{rd}$ trephine for ease of implant extraction. This approach can eliminate the need to do an extended osteotomy (ETO) for implant extraction. In the steps 700 illustrated in FIG. 7, the robot 102 may determine angles relative to the three-dimensional coordinate system 510 for approaching the previously implanted prosthetic knee 502 with the one or more surgical tools 120, and/or the robot 102 may generate one or more additional three-dimensional coordinate system 510 to align with the anatomical structures or the prosthetic structures being operated on in each step.

Figure 8:
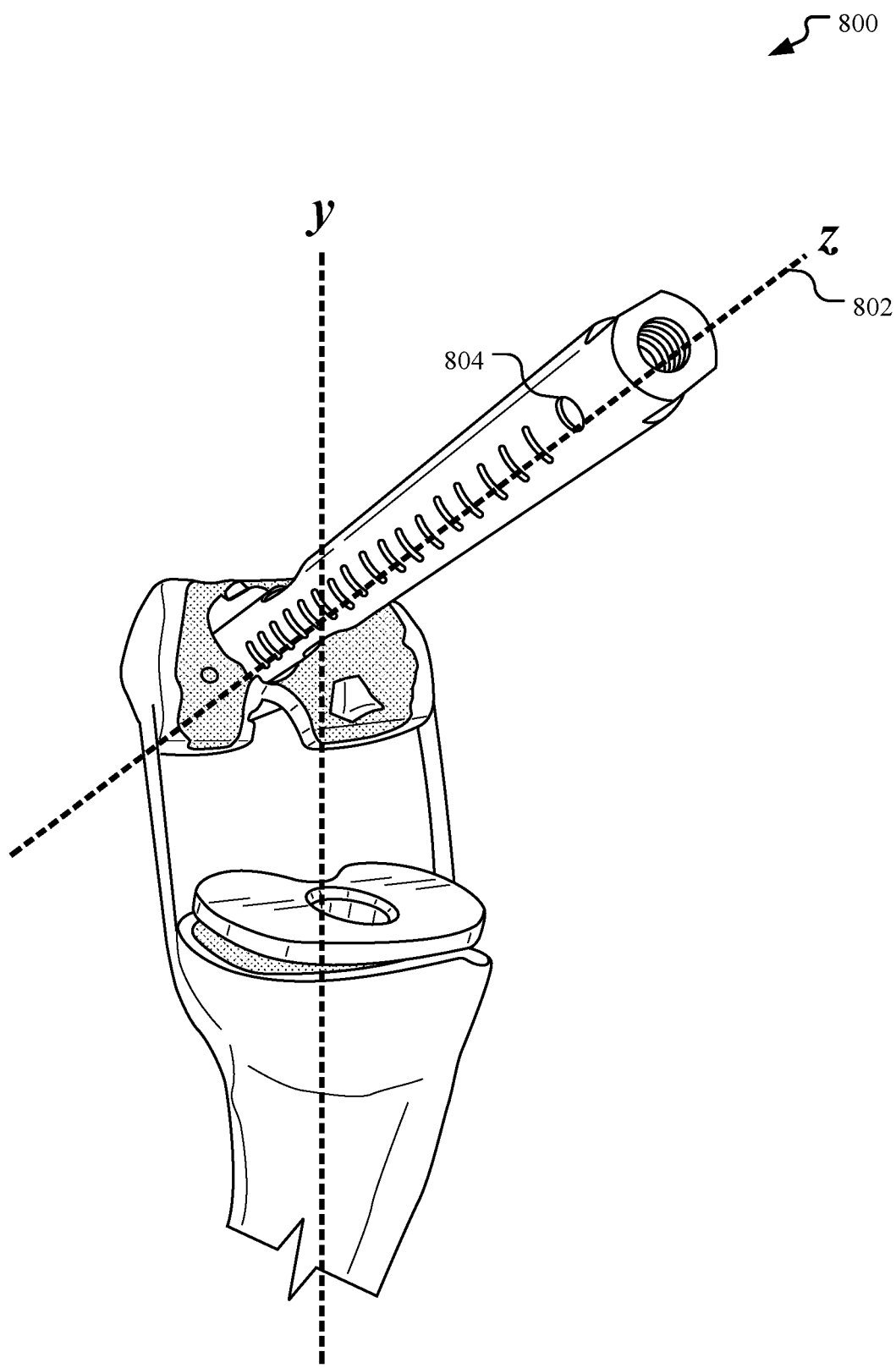
FIG. 8 is a drawing illustrating a step of an example method for robotic joint revision.

Referring to FIG. 8, a step 800 (e.g., the sixth step of the sequence of steps) for performing an example method for robotic joint revision is shown. FIG. 8 illustrates the utilization of the trephine reamer (e.g., a sixth tool) for removing a metal stem from the intermedullary canal of the femur, for instance, by approaching the metal stem or keel with the trephine reamer in a direction substantially parallel to a z-axis 802 of the three-dimensional coordinate system 510 This tool may attach to the robotic arm 114 to allow the surgeon more control in advancing the trephine reamer to remove the keel. The illustration of FIG. 8 shows a full cylinder 804, however the $\frac{1}{3}^{rd}$ trephine reamer may be used. Using the $\frac{1}{3}^{rd}$ trephine may eliminate over torqueing of the femur. The elasticity of bone is unique in any giving patient and having the option of a $\frac{1}{3}$rd trephine vs a full circle may give the surgeon more control of the amount of stresses associated with breaking the implant/bone or cement/implant interface.

In some examples, the sequence of steps may include a step for removing a tibial component, such as the tibial tray 506. A series of saws, burrs and osteotomes may be used to work around the tibial component to break the cement to bone interface or the cement to implant interface. With the robot 102, a surgeon can set the plane of the cutting devices to remove less bone and extract the implant based off of registration and implant thickness. In some instance, uniquely designed metal cutting burrs and saws may be used to cut a top of the tibia off of the 'keel' of the implant. There are several different types of keels on the market today. With this approach, the desired resection may be made, regardless of the keel geometry. Like the femur, there are parts of the bone/cement interface that a surgeon typically cannot access. Usually, it is directly behind the keel and the majority of the posterior aspect of the tibia. In the disclosed methods, the surgeon may use the robot 102 to cut the flat tray off, and may use a straight burr to debond the remaining cement left around the keel 508, while not removal the proximal tibia bone which establishes the joint line. Once the cement is broken around the remaining keel 508, the rest of the tibial component of the implant, including the keel 508, may be removed. Upon removing the hardware, an IM reamer may be used to prepare the stem on the revision component, the tibia is sized and a trial tibia may be placed on the tibia. At this point, a trial poly may be placed and the knee may be ranged to assess stability and tracking of the patella.

There may be significant advantages to a clean removal of a prosthetic implant, as discussed above. A few examples of removing too much bone with a previous implant, as may occur in typical implant removals that do not incorporate the techniques discussed herein, are: too much distal femur removal may result in loose extension gap/raises the joint line; too much posterior femur removal may result in loose flexion gap and can lead to a bigger femur; too much tibia removal may lower the joint line and affect flexion and extension balancing; and too much posterior tibia removal may result in a loose flexion gap. These challenges may lead to poor outcomes, mid flexion instability, multi-directional instability and early failure of the revision components. As patients are living longer, the demand for high performing implant revision components and techniques is rising. Massive bone loss from implant extraction can create a challenging revision for surgeons. With the use of robotics, such as the robot 102 with the robotic arm 114 and the methods discussed herein, the extraction of previous implants can be more predictable, which may lead to less bone loss and more reproducible outcomes.

What is claimed is:

1. A system for robotic joint revision surgery comprising:
   a robot including a plurality of components coupled via a connection, the plurality of components including:
   a robotic arm,
   a processor,
   a non-transitory computer readable medium,
   one or more output devices,
   a plurality of input devices, and
   an input/output interface; and
   one or more surgical tools interchangeably in connection with the robotic arm, the one or more surgical tools including at least one of:
   a large diameter cutting wheel,
   an in-line cutting tip,
   a posterior curved cradle,
   a reciprocal saw,
   a long burr,
   a hemispherical or ⅓ trephine reamer,
   a small osteotome operable to chip away at cement,
   a curved osteotome,
   a vibrator attachment,
   a bonding rotary tool,
   a keel remover,
   a motion converter,
   a bone cement melter, or a tapered drill;
wherein the robot is configured to remove a previous prosthetic joint from a bone of a patient by:
recognizing a first surgical tool of the one or more surgical tools by recognizing the large diameter cutting wheel,
navigating, via the robotic arm, the first surgical tool to cut a first portion of the previous prosthetic joint,
recognizing a second surgical tool of the one or more surgical tools by recognizing the long burr,
navigating, via the robotic arm, the second surgical tool to break a bone-cement interface around the previous prosthetic joint,
recognizing a third surgical tool of the one or more surgical tools by recognizing the tapered drill, and
navigating, via the robotic arm, the third surgical tool to drill into a second portion of the previous prosthetic joint.

2. The system of claim 1, wherein the plurality of input devices includes a plurality of sensors, a tracking ray, or a plurality of cameras.

3. The system of claim 1, wherein the plurality of input devices includes at least one of strain gauge, a tension gauge, or a patella tracking device.

4. The system of claim 1, wherein the one or more output devices includes a display unit.

5. The system of claim 1, wherein the one or more output devices is integral to other components of the plurality of components of the robot.

6. The system of claim 1, wherein the one or more output devices are separate from other components of the plurality of components of the robot.

7. The system of claim 1, wherein the plurality of input devices are integral to other components of the plurality of components of the robot.

8. The system of claim 1, wherein the plurality of input devices are separate from other components of the plurality of components of the robot.

9. The system of claim 1, wherein the large diameter cutting wheel has a diameter of 40-50 mm.

10. The system of claim 1, wherein the reciprocal saw has a thickness of at least 1.89 mm.

11. The system of claim 1, wherein the long burr has a length of 120-135 mm.

12. The system of claim 1, further comprising:
an adaptor bolt attached to the tapered drill; and
a slap hammer operable to attach to the adaptor bolt and extract at least a portion of the previous prosthetic joint.

13. The system of claim 1, wherein the processor is configured to:
receive a plurality of three-dimensional images of a limb of the patient having the previous prosthetic joint;
generate a surgical plan based on the plurality of three-dimensional images; and
execute instructions from the non-transitory computer readable medium in response to input from the plurality of input devices.

14. The system of claim 13, wherein the processor is configured to make changes to the surgical plan in response to the input from the plurality of input devices.

15. A system for robotic joint revision surgery comprising:
a robot with a robotic arm;
a processor;
a non-transitory computer readable medium;
one or more output devices;
a plurality of input devices;
an input/output interface; and
one or more surgical tools interchangeably in connection with the robotic arm, wherein the robot is configured to remove a previous prosthetic joint from a bone of a patient by:
recognizing a first surgical tool of the one or more surgical tools for cutting a first portion of the previous prosthetic joint,
navigating the first surgical tool to cut the first portion of the previous prosthetic joint,
recognizing a second surgical tool of the one or more surgical tools for breaking a bone-cement interface around the previous prosthetic joint,
navigating, via the robotic arm, the second surgical tool to break the bone-cement interface around the previous prosthetic joint,
recognizing a third surgical tool of the one or more surgical tools for drilling into a second portion of the previous prosthetic joint,
navigating, via the robotic arm, the third surgical tool to drill into the second portion of the previous prosthetic joint,
recognizing a fourth surgical tool by recognizing a slap hammer, and
extracting the previous prosthetic joint with the slap hammer.

16. A system for robotic joint revision surgery comprising:
a robot with a robotic arm;
a processor;
a non-transitory computer readable medium;
one or more output devices;
a plurality of input devices;
an input/output interface; and
one or more surgical tools interchangeably in connection with the robotic arm, wherein the robot is configured to remove a previous prosthetic joint from a bone of a patient by:
recognizing a first surgical tool of the one or more surgical tools for cutting the previous prosthetic joint,
navigating the first surgical tool to cut a portion of the previous prosthetic joint,
recognizing a second surgical tool of the one or more surgical tools by recognizing at least one of a long burr, a drill, or a slap hammer, and
navigating, the second surgical tool to perform a prosthetic joint removal operation after cutting the portion of the previous prosthetic joint with the first surgical tool.

* * * * *